(12) United States Patent
Liu et al.

(10) Patent No.: US 12,152,249 B2
(45) Date of Patent: Nov. 26, 2024

(54) METHOD FOR PREPARING MICROCARRIER SUITABLE FOR THREE-DIMENSIONAL CELL CULTURE AND REACTION APPARATUS

(71) Applicant: Beijing CytoNiche Biotechnology Co., Ltd., Beijing (CN)

(72) Inventors: Wei Liu, Beijing (CN); Xiaojun Yan, Beijing (CN)

(73) Assignee: Beijing CytoNiche Biotechnology Co., Ltd., Beijing (CN)

( * ) Notice: Subject to any disclaimer, the term of this patent is extended or adjusted under 35 U.S.C. 154(b) by 88 days.

(21) Appl. No.: 17/309,317

(22) PCT Filed: Oct. 15, 2020

(86) PCT No.: PCT/CN2020/121064
§ 371 (c)(1),
(2) Date: May 18, 2021

(87) PCT Pub. No.: WO2021/227353
PCT Pub. Date: Nov. 18, 2021

(65) Prior Publication Data
US 2023/0077045 A1    Mar. 9, 2023

(30) Foreign Application Priority Data

May 12, 2020    (CN) .......................... 202010395405.5

(51) Int. Cl.
*C08J 9/28* (2006.01)
*B01F 23/41* (2022.01)
(Continued)

(52) U.S. Cl.
CPC ........ *C12N 5/0075* (2013.01); *B01F 23/4105* (2022.01); *B01F 23/4143* (2022.01);
(Continued)

(58) Field of Classification Search
CPC .......................... C12N 5/0075; C12N 5/0062; C12N 2513/00; C12N 2531/00; C12N 2533/54;
(Continued)

(56) References Cited

U.S. PATENT DOCUMENTS

| | | | | | |
|---|---|---|---|---|---|
| 4,530,840 | A | * | 7/1985 | Tice | A61K 9/1647 514/180 |
| 2011/0204533 | A1 | * | 8/2011 | Winchester | B01F 25/4523 425/5 |
| 2016/0083690 | A1 | | 3/2016 | Birch et al. | |

FOREIGN PATENT DOCUMENTS

| | | |
|---|---|---|
| CN | 1318429 A | 10/2001 |
| CN | 1454703 A | 11/2003 |
| CN | 101683592 A | 3/2010 |
| CN | 102794119 A | 11/2012 |
| CN | 103182278 A | 7/2013 |
| CN | 109762802 A | 5/2019 |

(Continued)

OTHER PUBLICATIONS

SIPO, International Search Report issued in IA No. PCT/CN2020/121064, mailed Feb. 18, 2021.

*Primary Examiner* — Robert S Jones, Jr.
*Assistant Examiner* — Jiangtian Xu
(74) *Attorney, Agent, or Firm* — LKGlobal | Lorenz & Kopf, LLP

(57) ABSTRACT

Provided herein is a method for preparing microcarrier particles, comprising the steps of allowing the dispersed phase liquid flow through a multi-hole plate at a low temperature to form liquid microspheres in a continuous phase, and enabling a synthetic polymer and/or natural biological macromolecules within the liquid microspheres to be subject to a curing reaction at a low temperature to form particles. Further provided herein are the method for preparing an emulsion and an apparatus and process system for preparing microcarrier particles, which can be used for preparing emulsions and microcarrier particles on a large scale.

12 Claims, 3 Drawing Sheets

(51) Int. Cl.
    *B01F 23/80*     (2022.01)
    *C08L 89/00*     (2006.01)
    *C12N 5/00*     (2006.01)
    *B01F 101/44*     (2022.01)
    *C09K 23/00*     (2022.01)

(52) U.S. Cl.
    CPC ........ *B01F 23/4145* (2022.01); *B01F 23/808* (2022.01); *C08J 9/28* (2013.01); *C08L 89/00* (2013.01); *C12N 5/0062* (2013.01); *B01F 2101/44* (2022.01); *C08J 2201/0484* (2013.01); *C08J 2389/00* (2013.01); *C08J 2405/04* (2013.01); *C09K 23/00* (2022.01); *C12N 2513/00* (2013.01); *C12N 2531/00* (2013.01); *C12N 2533/54* (2013.01); *C12N 2533/74* (2013.01)

(58) Field of Classification Search
    CPC ............. C12N 2533/74; B01F 23/4143; B01F 23/4145; B01F 23/4105; B01F 23/808; B01F 2101/44; C08J 9/28; C08J 2201/0484; C08J 2389/00; C08J 2405/04; C08L 89/00; C09K 23/00
    See application file for complete search history.

(56) References Cited

FOREIGN PATENT DOCUMENTS

| | | | |
|---|---|---|---|
| EP | 2944370 A1 | 11/2015 | |
| JP | 2006021111 A | 1/2006 | |
| JP | 6416206 B2 | 10/2018 | |
| WO | WO-2014104369 A1 * | 7/2014 | ............ B01F 3/0807 |

* cited by examiner

METHOD FOR PREPARING MICROCARRIER SUITABLE FOR THREE-DIMENSIONAL CELL CULTURE AND REACTION APPARATUS

CROSS-REFERENCE TO RELATED APPLICATION

This application is a U.S. National-Stage entry under 35 U.S.C. § 371 based on International Application No. PCT/CN2020/121064, filed Oct. 15, 2020, which was published under PCT Article 21(2) and which claims priority to Chinese Application No. 202010395405.5, filed May 12, 2020, which are all hereby incorporated in their entirety by reference.

TECHNICAL FIELD

The present disclosure relates to a preparation method and apparatus of microcarriers, and more particularly to a method and process system for preparing microcarriers on a large scale.

BACKGROUND

The 3D TableTrix Microcarrier Tablet (produced by Beijing CytoNiche Biotech Ltd.) is a novel cell expansion carrier material customized for stem cell production. This technical product employs the innovative design of a microcarrier tablet, and each microcarrier tablet is definite in weight, independently sterilized and ready-to-use, such that cumbersome operations required by conventional microcarriers such as weighing and sterilization are omitted, and this product is superior to the conventional microcarriers for cell culture.

The microcarrier can be prepared in the form of microcarrier tablet. The microcarrier tablet can be dispersed into tens of thousands of elastic three-dimensional porous microcarrier particles in the presence of water, and the 3D structure and physical properties of the dispersed elastic microcarrier are kept unchanged compared with those of the microcarrier which is not made into the microcarrier tablet. The porosity of the microcarrier is more than about 90%, and particle size of 50-500 μm could be produced with uniformity controlled within 100 μm. Moreover, the biochemical and physical properties can be customized, to realize accurate and controllable 3D biomimetic culture. Currently, its raw materials are of pharmaceutical grade to meet clinical application standards. When used in conjunction with reagents such as 3D FloTrix Digest (produced by Beijing CytoNiche Biotech Ltd.), mild and nondestructive recovery of cells from 3D TableTrix Microcarrier Tablet can be achieved by fully lysis of microcarriers, without any residual harmful substance in the final cell product.

In view of the large market demand for such microcarrier tablet and the limited throughput in existing production mode, there is an urgent need for new methods and apparatuses to scale up the production. In addition, other objects, desirable features and characteristics will become apparent from the subsequent summary and detailed description, and the appended claims, taken in conjunction with the accompanying drawings and this background.

SUMMARY

In one aspect, provided herein is a method for preparing an emulsion, comprising the steps of allowing a dispersed phase liquid to flow from one side to the other side of a multi-hole plate through a plurality of micro-wells of the multi-hole plate while allowing a continuous phase liquid to flow, parallel to the multi-hole plate, on the other side of the multi-hole plate, shearing the dispersed phase liquid passing through the multi-hole plate to form liquid microspheres in the flowing continuous phase liquid.

In some embodiments, the micro-wells have a diameter between 0.1 μm and 500 μm.

In some embodiments, the micro-wells have a diameter between 30 μm and 50 μm.

In some embodiments, the emulsion is a water-in-oil emulsion.

In some embodiments, the size of liquid microspheres is adjusted by adjusting the flow rate of dispersed phase liquid and/or continuous phase liquid.

In one aspect, provided herein is a method for preparing microcarrier particles, comprising the steps:
1) preparing a dispersed phase liquid and a continuous phase liquid, wherein:
    the dispersed phase liquid contains a synthetic polymer and/or natural biological macromolecules; and a curing agent; and
    the continuous phase liquid contains an organic solvent and a nonionic surfactant.
2) allowing the dispersed phase liquid to flow from one side of a multi-hole plate to the other side of the multi-hole plate through a plurality of micro-wells of the multi-hole plate while allowing the continuous phase liquid to flow, parallel to the multi-hole plate, on the other side of the multi-hole plate, shearing the dispersed phase liquid passing through the multi-hole plate to form liquid microspheres in the flowing continuous phase liquid;
3) making the synthetic polymer and/or natural biological macromolecules in the liquid microsphere react with the curing agent to form particles; and
4) collecting and washing the particles;
    wherein, the temperature of the continuous phase liquid in Step 2) does not exceed 0° C.; Step 3) is executed for 2-72 hours at the temperature of not higher than 0° C.

In some embodiments, Step 2) is executed in a vessel comprising the multi-hole plate which separates the interior of the vessel into a first portion and a second portion, the dispersed phase liquid enters the first portion through a dispersed phase inlet arranged on the vessel and connected with the first portion and then flows into the second portion through the multi-hole plate; the continuous phase liquid enters the second portion through a continuous phase inlet arranged on the vessel and connected with the second portion; the mixed liquid containing the liquid microspheres after the dispersed phase liquid and the continuous phase liquid are mixed leaves the vessel through an outlet arranged on the vessel and connected with the second portion; and the vessel outlet and the continuous phase inlet are arranged on the opposite sides of the vessel.

In some embodiments, the dispersed phase liquid enters the first portion of the vessel and flows through the multi-hole plate by gas pressurization; the continuous phase liquid enters the second portion of the vessel by a gear pump and flows parallel to the multi-hole plate.

In some embodiments, Step 3) is performed in a tank provided with a stirring device.

In some embodiments, Step 4) is performed by vacuuming in a tank provided with a filtering device.

In some embodiments, the micro-wells have a diameter between 0.1 μm and 500 μm.

In some embodiments, the micro-wells have a diameter between 30 μm and 50 μm.

In some embodiments, the flow of the continuous phase liquid is 5-20 times that of the dispersed phase liquid over the same time.

In some embodiments, the synthetic polymer is selected from at least one of polyethylene glycol, a polyethylene glycol derivative, polyethylene glycol diacrylate, polypropylene, polystyrene, polyacrylamide, polylactic acid, polyhydroxy acid, a polylactic acid-alcohol acid copolymer, polydimethylsiloxane, polyanhydride, polyacrylate, polyamide, polyamino acid, polyacetal, polycyanoacrylate, polyurethane, polypyrrole, polyester, polymethacrylate, polyethylene, polycarbonate, and a polyethylene oxide.

In some embodiments, the natural biological macromolecules are selected from at least one of collagen, proteoglycan, glycoprotein, gelatin, a gelatin derivative, chitin, alginate, an alginate derivative, agar, fibrinogen, matrigel, a hyaluronic acid, laminin, and fibronectin.

In some embodiments, the organic solvent is selected from at least one of hydrofluoroether, carbon tetrachloride, petroleum ether, cyclohexane, liquid paraffin, edible oil, soybean oil, olive oil, chloroform, dichloromethane, carbon tetrachloride, and tetrachloroethylene.

In some embodiments, the nonionic surfactant is selected from at least one of sorbitan fatty acid ester, fatty glyceride, laurate, alkylphenol polyoxyethylene ether, high-carbon fatty alcohol-polyoxyethylene ether, arlacel, PO-500, polyoxyethylene sorbitan monooleate, and tween.

In some embodiments, the curing agent is selected from at least one of divinylbenzene, diisocyanate, N-hydroxysuccinimide, N,N-methylenebisacrylamide, formaldehyde, glutaraldehyde, 1-(3-dimethylaminopropyl)-3-ethylcarbodiimide hydrochloride, calcium ions, tetramethylethylenediamine, ammonium sulfate, genipin, and transglutaminase.

In some embodiments, the dispersed phase liquid further contains a buffer agent selected from at least one of carboxymethylcellulose, sodium chloride, polyacrylamide, potassium chloride, polyvinylpyrrolidone, sodium sulfate, calcium chloride, sodium chloride, sodium carbonate, and sodium bicarbonate.

In some embodiments, the method further comprises the step of washing the particles with a cleaning agent selected from at least one of acetone, anhydrous copper sulfate, calcium chloride, sodium sulfate, anhydrous ethanol, medical alcohol, hydrofluoroether, sodium alkylbenzene sulfonate, sodium aliphatic alcohol sulfate, sodium tripolyphosphate, and deionized water.

In some embodiments, the ratio of the organic solvent to the nonionic surfactant in the continuous phase liquid is from 5:1 to 20:1 by weight.

In another aspect, provided herein is an apparatus for preparing an emulsion, comprising:
1) a vessel;
2) a multi-hole plate arranged in the vessel and including a plurality of micro-wells; the multi-hole plate separating the interior of the first vessel into a first portion and a second portion;
3) a dispersed phase inlet connected with the first portion and used for feeding a dispersed phase liquid;
4) a continuous phase inlet connected with the second portion and used for feeding a continuous phase liquid; and
5) a vessel outlet connected with the second portion.
wherein, the vessel outlet and the continuous phase inlet are arranged on opposite sides of the vessel, such that the continuous phase liquid fed from the continuous phase inlet can flow through the second portion in a direction parallel to the multi-hole plate and then flow out from the vessel outlet.

In some embodiments, the micro-wells have a diameter between 0.1 μm and 500 μm.

In some embodiments, the micro-wells have a diameter between 30 μm and 50 μm.

In some embodiments, the vessel is in a cuboid shape.

In some embodiments, the number of continuous phase inlets is two or more, and the number of vessel outlets is also two or more.

In some embodiments, the continuous phase inlet and the vessel outlet have the same height relative to the vessel bottom.

In some embodiments, the emulsion is a water-in-oil emulsion.

In another aspect, provided herein is a process system for preparing microcarrier particles, comprising:
1) an apparatus for preparing an emulsion, comprising:
  a vessel;
  a multi-hole plate arranged in the vessel and including a plurality of micro-wells; the multi-hole plate separating the interior of the first vessel into a first portion and a second portion;
  a dispersed phase inlet connected with the first portion and used for feeding a dispersed phase liquid;
  a continuous phase inlet connected with the second portion and used for feeding a continuous phase liquid; and
  a vessel outlet connected with the second portion.
  wherein, the vessel outlet and the continuous phase inlet are arranged on opposite sides of the vessel, such that the continuous phase liquid fed from the continuous phase inlet can flow through the second portion in a direction parallel to the multi-hole plate and then flow out from the vessel outlet;
2) a first tank connected with the dispersed phase inlet and used for containing the dispersed phase liquid, wherein the first tank is further connected with a pressurizing device or a gas cylinder so as to enable the dispersed phase liquid to enter the apparatus for preparing the emulsion under pressure;
3) a second tank connected with the continuous phase inlet and provided with a cooling device, used for containing the continuous phase liquid and cooling the continuous phase liquid;
4) a third tank connected with the vessel outlet, wherein the third tank is provided with a stirrer and a cooling device and used for carrying out emulsion reaction; and
5) a fourth tank connected with the third tank, wherein the fourth tank is provided with a filtering device for collecting particles formed by the emulsion reaction.

In some embodiments, the vessel is in a cuboid shape.

In some embodiments, the number of continuous phase inlets is two or more, and the number of vessel outlets is also two or more.

In some embodiments, the continuous phase inlet and the vessel outlet have the same height relative to the vessel bottom.

In some embodiments, a gear pump is arranged between the continuous phase inlet and the second tank and used for feeding the continuous phase liquid from the second tank to the apparatus for preparing the emulsion.

In some embodiments, the process elution further comprises a fifth tank connected with the fourth tank, wherein the fifth tank is provided with a filtering device for washing the particles.

In some embodiments, the fourth tank and the fifth tank are each provided with an evacuating device.

In some embodiments, the micro-wells have a diameter between 0.1 μm and 500 μm.

In some embodiments, the micro-wells have a diameter between 30 μm and 50 μm.

The method and the apparatus provided by the present disclosure can be used to prepare emulsions as well as microcarrier particles on a large scale.

BRIEF DESCRIPTION OF THE DRAWINGS

The present disclosure will hereinafter be described in conjunction with the following drawing figures, wherein like numerals denote like elements, and.

DETAILED DESCRIPTION

Figure 1:
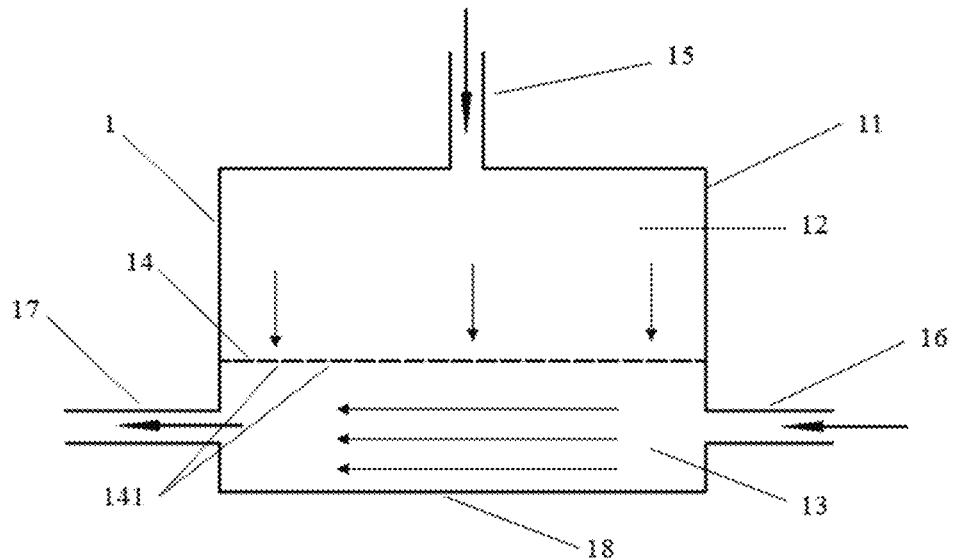
FIG. 1 is a schematic structural view of an apparatus for preparing an emulsion (or a microsphere forming machine).

The following detailed description is merely exemplary in nature and is not intended to limit the disclosure or the application and uses of the disclosure. Furthermore, there is no intention to be bound by any theory presented in the preceding background of the disclosure or the following detailed description.

Unless otherwise defined, all terms (including technical and scientific terms) used herein have the same meaning as commonly understood by a typical technical personnel practicing the art.

The term "emulsion", also referred to as an emulsified liquid, is a dispersion system formed by two immiscible liquids, in which the liquid in the form of suspended droplets is referred to as a dispersed phase (or internal phase) and the continuously distributed liquid as a dispersion medium is referred to as a continuous phase (or external phase). A large number of organic substances immiscible with water exist in nature, and many emulsions consist of a water phase (containing a main component: water or water-soluble component) and an organic phase (containing a main component: water-insoluble organic substance, also known as an oil phase). Generally, an emulsion having a water phase as the dispersed phase and an organic phase as the continuous phase is referred to as a "water-in-oil emulsion". Correspondingly, an emulsion having an organic phase as the dispersed phase and a water phase as the continuous phase is referred to as an "oil-in-water emulsion". Suspended droplets of a dispersed phase liquid formed in a continuous phase liquid are also referred to as "liquid microspheres" herein.

The term "emulsion reaction" as used herein refers to a chemical reaction among components within the liquid microspheres. For example, in the preparation process of microcarrier particles described below, particles insoluble in water and organic phases are obtained by curing a macromolecular compound, such as a synthetic polymer, within the liquid microspheres.

The term "multi-hole plate" as used herein refers to a plate having a plurality of micro-wells formed therein. In the method and apparatus provided by the present disclosure, a "multi-hole plate" is used to restrict the flow of dispersed phase liquid such that the dispersed phase liquid can pass from one side to the other side of the multi-hole plate only through the plurality of micro-wells. Therefore, the multi-hole plate is not limited to a specific shape in terms of use, and may even be in an irregular shape as long as this purpose can be achieved. However, a plate-like shape is preferred for preparation of the emulsion, because it not only facilitates processing, but also is conductive to formation of uniform size of liquid microspheres. Generally, the micro-wells have a diameter between 0.1 μm and 500 μm. When the multi-hole plate has a considerable thickness, a micro-well is actually a microtube having a certain length, however, for the sake of brevity, the term "micro-well" also means such microtube. Similarly, the present disclosure does not particularly limit the material of the micro-well plate as long as the above purpose can be achieved and the dispersed phase liquid and the continuous phase liquid are chemically inert, for example, plastics, ceramics and other materials may be used.

It is mentioned herein that the continuous phase is allowed to flow "parallel" to the multi-hole plate in the apparatus for preparing an emulsion. Ideally, the dispersed phase liquid flows, perpendicular to the multi-hole plate, through the micro-wells, and the continuous phase liquid flows perpendicular to the dispersed phase liquid flow through the micro-wells (i.e., parallel to the multi-hole plate), thereby cutting the dispersed phase liquid flow into liquid microspheres. Of course, those skilled in the art will appreciate that in most cases, if it is not strict for parallel flowing, the purpose that the continuous phase liquid cuts the dispersed phase liquid flow into liquid microspheres may also be achieved. Thus, during emulsion formation, in most cases, it is sufficient to have a continuous phase liquid inlet and a continuous phase liquid outlet on the apparatus for preparing the emulsion arranged on opposite sides thereof i.e., "opposite arrangement". In some embodiments, the continuous phase liquid inlet and the continuous phase liquid outlet have the same height. In some embodiments, a plurality of continuous phase liquid inlets and a plurality of vessel outlets may be arranged horizontally on the opposite sides of an approximately cube-shaped vessel to facilitate parallel flowing of the continuous phase liquid.

The term "microcarrier particles" or "microcarriers" refer to particles having a size in the micron-scale range, which are suitable for the growth of cells attached thereto. The size of microcarrier particles is preferably between 50 μm and 500 μm. The porosity is generally more than 80%, e.g., 90% or 95%. As most cells can only proliferated by attaching to the surface of a solid substrate, hence microcarriers havinge characteristics such as porous, large surface area, biocompatibility and the like, which allow cells to grow inside the microcarriers, such as those prepared by the present disclosure, to form a three-dimensional culture model, and such bionic three-dimensional culture method is gaining more applications.

The term "large scale" means that the amount of a prepared product can meet the demand of laboratory research or even industrial production needs. For example, about 1 mL to 1,000 L (such as 5 mL to 100 L, 100 mL to 10 L and 500 mL to 1 L) or even more emulsion may be prepared at a time. For microcarrier particles, the term "large scale" means, for example, preparing 1 mg to 1,000 kg (such as 100 mg to 100 kg, 1 g to 10 kg and 200 g to 1 kg) or even more at a time.

In some aspects of the present disclosure, provided is a method for preparing an emulsion, which can be used to perform large-scale emulsion preparation. The method comprises the steps of allowing a dispersed phase liquid to flow from one side to the other side of a multi-hole plate through a plurality of micro-wells of the multi-hole plate while allowing a continuous phase liquid to flow, parallel to the multi-hole plate, on the other side of the multi-hole plate, shearing the dispersed phase liquid passing through the multi-hole plate to form liquid microspheres in the flowing continuous phase liquid. Since a plurality of micro-wells may be densely arranged on the multi-hole plate, a large amount of emulsion can be continuously and rapidly prepared by cross-flowing of the dispersed phase liquid and the continuous phase liquid in a substantially perpendicular direction in the vicinity of the multi-hole plate.

In some specific embodiments, the emulsion formation process is carried out in a vessel comprising a multi-hole plate. In more detail, the multi-hole plate arranged inside the vessel separates the interior of the vessel into a first portion and a second portion, the dispersed phase liquid enters the first portion through a dispersed phase inlet arranged on the vessel and connected with the first portion and then flows into the second portion through the multi-hole plate; the continuous phase liquid enters the second portion through a continuous phase inlet arranged on the vessel and connected with the second portion; and the mixed liquid containing the liquid microspheres after the dispersed phase liquid and the continuous phase liquid are mixed leaves the vessel through a vessel outlet arranged on the vessel and connected with the second portion. To allow the continuous phase to pass, substantially parallel to the multi-hole plate, through the second portion, the vessel outlet and the continuous phase inlet are arranged on opposite sides of the vessel.

Generally, the use amount of dispersed phase liquid is not more than that of the continuous phase liquid, for example, in the prepared emulsion, the ratio of the dispersed phase liquid to the mobile phase liquid is 1:1 to 1:30, preferably 1:5 to 1:20. If it is out of this range, the yield of the final product may be affected. The size of liquid microspheres may be controlled by adjusting that of micro-wells. In addition, the flow rates of the dispersed phase and continuous phase as well as the relative flow rate thereof may also affect the size of liquid microspheres. To allow the dispersed phase liquid and the continuous phase liquid to flow at a constant speed substantially, liquid flowing may be controlled by using a pressurized gas or a device such as a gear pump. For example, in a specific embodiment, the dispersed phase liquid is forced to flow at a constant speed by gas pressurization, and the continuous phase liquid is forced to flow at a constant speed by rotation of a gear pump. In some embodiments of the present disclosure, the dispersed phase is a water phase containing reactants, and the continuous phase is an organic phase containing organic substances.

Using the emulsion forming process described above, the present disclosure also provides a method for preparing microcarrier particles, which is suitable for large-scale preparation of microcarrier particles. A dispersed phase liquid used in this method contains a compound to be cured (such as a synthetic polymer and/or natural biological macromolecules) and a curing agent. A continuous phase liquid used contains an organic solvent and a nonionic surfactant. The liquid microspheres generated by the emulsion forming process react under a stirring condition to form particles. The particles are then collected by filtration and washed with a cleaning agent.

The inventors have found that particles prepared by the above-described emulsion forming process and reaction process carried out at a low temperature (0° C. or below, such as −10° C. or below, such as −30° C.) have better porosity and larger specific surface area, and are more suitable as a three-dimensional carrier for cell culture. Generally, the lower the temperature is, the smaller the pore size of prepared microcarrier particles is. For example, the microcarrier particles prepared by reaction at −30° C. have a pore size between 5 μm and 20 μm approximately.

To allow the dispersed phase liquid and the continuous phase liquid to flow at a constant speed substantially, liquid flowing may be controlled by using a pressurized gas or a device such as a gear pump. For example, in a specific embodiment, the dispersed phase liquid is forced to flow at a constant speed by gas pressurization, and the continuous phase liquid is forced to flow at a constant speed by rotation of a gear pump. Generally, the greater the pressure intensity to which the dispersed phase is subjected, the faster the flow rate is, the larger the particle size of prepared microcarrier particles is, and vice versa. In addition, the lower the flow rate of continuous phase is, the larger the particle size of prepared microcarrier particles, and vice versa. Therefore, the particle size of finally prepared microcarrier particles can be adjusted by flexibly controlling the diameter of the wells on the multi-hole plate and the flow rates of the dispersed phase liquid and the continuous phase liquid.

As an example, the synthetic polymer includes at least one of polyethylene glycol, a polyethylene glycol derivative, polyethylene glycol diacrylate, polypropylene, polystyrene, polyacrylamide, polylactic acid, polyhydroxy acid, a polylactic acid-alcohol acid copolymer, polydimethylsiloxane, polyanhydride, polyacrylate, polyamide, polyamino acid, polyacetal, polycyanoacrylate, polyurethane, polypyrrole, polyester, polymethacrylate, polyethylene, polycarbonate, and a polyethylene oxide.

As an example, the natural biological macromolecules include at least one of collagen, proteoglycan, glycoprotein, gelatin, a gelatin derivative, chitin, alginate, an alginate derivative, agar, fibrinogen, matrigel, a hyaluronic acid, laminin, and fibronectin.

As an example, the curing agent includes at least one of divinylbenzene, diisocyanate, N-hydroxysuccinimide, N,N-methylenebisacrylamide, formaldehyde, glutaraldehyde, 1-(3-dimethylaminopropyl)-3-ethylcarbodiimide hydrochloride, calcium ions, tetramethylethylenediamine, ammonium sulfate, genipin, and transglutaminase.

As an example, the organic solvent includes at least one of hydrofluoroether, carbon tetrachloride, petroleum ether, cyclohexane, liquid paraffin, edible oil, soybean oil, olive oil, chloroform, dichloromethane, carbon tetrachloride, and tetrachloroethylene.

As an example, the nonionic surfactant includes at least one of sorbitan fatty acid ester, fatty glyceride, laurate, alkylphenol polyoxyethylene ether, high-carbon fatty alcohol-polyoxyethylene ether, arlacel, PO-500, polyoxyethylene sorbitan monooleate, and tween.

As an example, the cleaning agent adopted for washing particles includes at least one of acetone, anhydrous copper sulfate, calcium chloride, sodium sulfate, anhydrous ethanol, medical alcohol, hydrofluoroether, sodium alkylbenzene sulfonate, sodium aliphatic alcohol sulfate, sodium tripolyphosphate, and deionized water.

In some embodiments, the dispersed phase liquid further comprises a buffer agent. As an example, the buffer agent includes at least one of carboxymethylcellulose, sodium chloride, polyacrylamide, potassium chloride, polyvinylpyrrolidone, sodium sulfate, calcium chloride, sodium chloride, sodium carbonate, and sodium bicarbonate.

Generally, the concentration of the compound to be cured in the dispersed phase is between 1% and 20% (wt), and the amount of the curing agent used may be adjusted depending on the properties of the compound to be cured and the properties of the curing agent itself.

It should be noted that the above components listed as examples only are a portion of raw materials suitable for preparation of microcarrier particles, and those skilled in the art will readily substitute one or more of these substances with other similar substances according to their physical and chemical properties, and perform simple experiments to verify the feasibility according to the methods provided by the present disclosure. It will be apparent that methods for preparing microcarrier particles by adopting alternatives according to the methods provided by the present disclosure and products thereof are also within the scope of the present disclosure.

In some aspects, the present disclosure further provides an apparatus for preparing an emulsion, which can be used for preparing emulsions on a large scale. The apparatus for preparing the emulsion comprises:

a vessel;
a multi-hole plate arranged in the vessel and including a plurality of micro-wells; the multi-hole plate separating the interior of the first vessel into a first portion and a second portion;
a dispersed phase inlet connected with the first portion and used for feeding a dispersed phase liquid;
a continuous phase inlet connected with the second portion and used for feeding a continuous phase liquid; and
a vessel outlet connected with the second portion.
wherein, the vessel outlet and the continuous phase inlet are arranged on opposite sides of the vessel, such that the continuous phase liquid fed from the continuous phase inlet can flow through the second portion in a direction parallel to the multi-hole plate and then flow out from the vessel outlet.

Figure 2:
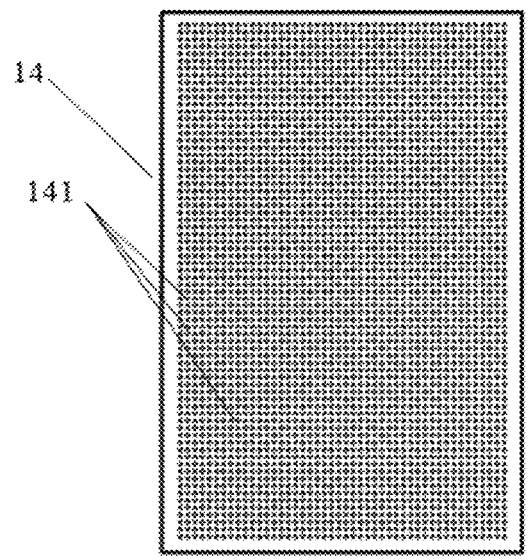
FIG. 2 is a schematic structural view of a multi-hole plate.

FIG. 1 is a cross-sectional view of a main body structure of the apparatus for preparing the emulsion of the present disclosure, schematically showing some structures of the apparatus for preparing the emulsion and various liquid flowing directions. As shown in FIG. 1, the vessel 1 comprises an internal space defined by the vessel wall 11, which is separated into an upper-side first portion 12 and a lower-side second portion 13 by the multi-hole plate 14 arranged in the vessel 1. The vessel 1 is provided with the dispersed phase inlet 15 connected with the first portion 12, the continuous phase inlet 16 connected with the second portion 13, and the vessel outlet 17. The continuous phase inlet 16 and the vessel outlet 17 are arranged on both sides of the vessel 1, respectively. In some embodiments, the continuous phase inlet 16 is substantially at the same height as the vessel outlet 17 relative to the bottom 18 of the vessel 1. The multi-hole plate 14 is provided with a plurality of micro-wells 141 (see FIG. 2). The dispersed phase liquid may be fed from the dispersed phase inlet 15 into the first portion 12 by pressurization, and under a pressure, the dispersed phase liquid will continue to flow through the micro-wells 141 of the multi-hole plate 14 into the lower-side second portion 13. Simultaneously, the continuous phase liquid enters the second portion 13 through the continuous phase inlet 16, flows substantially parallel to the multi-hole plate 14, and flows out from the vessel outlet 17. On the lower side of the multi-hole plate 14, the flowing continuous phase liquid shears the dispersed phase liquid passing through the micro-wells 141 of the multi-hole plate 14 into liquid microspheres insoluble in the continuous phase liquid, thereby forming a plurality of liquid microspheres suspended in the continuous phase liquid. These liquid microspheres leave from the vessel outlet 17 as the continuous phase flows. The liquid mixture flowing out from the vessel outlet 17 is collected, namely the prepared emulsion is obtained.

The diameter of micro-wells 141 of the multi-hole plate 14 may be adjusted in order to obtain liquid microspheres of a suitable size. When the diameter of the micro-wells is between 0.1 μm and 500 μm, 1-1,000 μm uniform liquid microspheres with particle size errors within the range of 100 μm can be prepared.

In some embodiments, the dispersed phase liquid is a water phase liquid, the continuous phase liquid is an organic phase liquid, and the prepared emulsion is a water-in-oil emulsion.

In some aspects, the present disclosure provides a process system for preparing microcarrier particles, which is used for preparing microcarrier particles on a large scale. The process system further comprises a plurality of tanks in addition to an apparatus for preparing an emulsion described above.

One of the tanks is connected with the dispersed phase inlet and used for containing the dispersed phase liquid. The tank may be provided with a stirrer for preparing a dispersed phase liquid, and may also be connected to a pressurizing device or a gas cylinder containing a compressed gas, and the dispersed phase liquid is introduced into the apparatus for preparing the emulsion by pressurizing the tank. The gas used should not react with the dispersed phase liquid and the continuous phase liquid and may, for example, be selected from the group consisting of air, nitrogen, carbon dioxide, oxygen, argon, etc. The pressure intensity of the gas used may be, for example, 1-100 Kpa.

Another one of the tanks is connected with the continuous phase inlet and used for containing the continuous phase liquid and cooling the continuous phase liquid. This tank may also be used for preparing the continuous phase liquid or cooling the prepared continuous phase liquid after fed into the tank. Methods for reducing the temperature of tank contents are well known in the art, for example, by providing a jacket for the tank and circulating a refrigerant liquid in the jacket by a refrigerator. The refrigerant liquid may include, for example, at least one of liquid nitrogen, ethanol, trichloroethane, isopropanol, dichloromethane, ethyl acetate, ethylene glycol, propylene glycol, isobutane, n-hexane, chloroform, tetrahydrofuran, bromohexane and acetonitrile.

Another one of the tanks is connected with the vessel outlet and can receive mixed liquid comprising liquid microspheres flowing out of the apparatus for preparing the emulsion. The tank is provided with a stirrer and a refrigerator, and allows reactants (such as biological macromolecules and a corresponding curing agent) contained in the liquid microspheres to react under a low temperature (such as −10° C.) to form particles.

Another one of the tanks is used for separating the formed particles from the mixed liquid. A filtering device, such as a vacuum filter, may be arranged in the tank, so that liquid components can be conveniently removed by vacuumizing with a vacuum pump, and the particles are left.

Optionally, a tank for washing particles may be further included. The tank may also be provided with a vacuum filter, and particles are washed repeatedly (such as 3-5 times) by vacuumizing after a cleaning agent is added into the tank.

Figure 3:
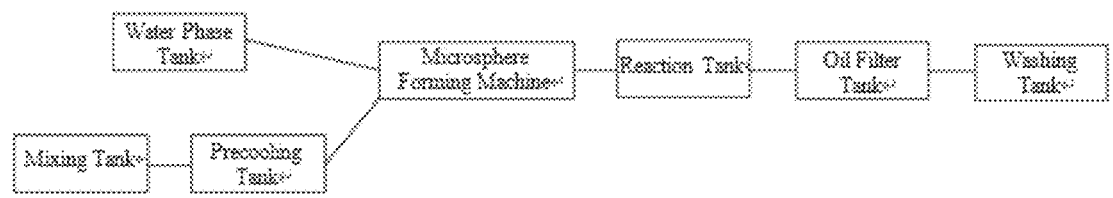
FIG. 3 shows various devices and connections involved in a process system for preparing microcarrier particles.

In a specific embodiment, the process system for preparing microcarrier particles of the present disclosure is as shown in FIG. 3. In the process system, a mixing tank is used for preparing a continuous phase liquid (organic phase), and after preparation, the continuous phase liquid may be transferred, for example, under a pressure, to a precooling tank provided with a refrigerator, where the continuous phase liquid is cooled to 0° C. or below (such as −10° C. or below). A water phase tank is used for preparing a dispersed phase liquid. The prepared dispersed phase liquid and the prepared continuous phase liquid are respectively delivered to an apparatus for preparing an emulsion under a pressure by a pump. The emulsion containing liquid microspheres generated in the apparatus for preparing the emulsion is then transferred to a reaction tank for emulsion reaction. Particles generated by the reaction are then separated from the other components of the emulsion by vacuum filtration in an oil filter tank. Finally, microcarrier particles are obtained after washing by a cleaning agent in a washing tank.

The structure and operating mode of the process system described above will now be described in further detail with reference to FIG. 3.

The system includes six tanks, namely the mixing tank, the precooling tank, the water phase tank, the reaction tank, the oil filter tank and the washing tank, which form a main body, cooperatively used other devices such as a vacuum pump, a cooling-water machine and a control panel, a plurality of connecting pipelines among the tanks, and externally connected delivery pipelines, such as those for drinking water, purified water, injection water, compressed air, high-temperature steam. Besides part of valves and connections, the whole system is made of 316L stainless steel to ensure that portions in contact with materials are all made of 316L stainless steel, and to avoid introduction of other impurities.

The tanks are arranged in a left-right mode depending on the process steps, and the height positions of part of the tanks are determined according to important process control points and embodied in the form of a workbench. Each device is briefly described in Table 1.

TABLE 1

Brief description on the tanks and other related devices

| Tank | Brief description |
|---|---|
| Mixing tank | 1. This mixing tank adopts a movable design, so that proportioning and cleaning of an oil phase is more convenient;<br>2. It is provided with a compressed air connector, so that it is effectively linked with other fixed tanks for subsequent treatment of materials;<br>3. Its motor adopts a full-sealing structure, so that the full-sealing function of the tank is effectively realized;<br>4. It is provided with a densimeter, so that the density of materials can be observed in real time. |
| Precooling tank | 1. This tank is provided with a densimeter, so that the density of materials can be observed in real time;<br>2. It is provided with two ports of compressed air and steam, so that device cleaning and online sterilization are effectively realized;<br>3. It adopts a bottom feeding mode, so that the phenomena of loss of materials due to attachment to the wall and the like are effectively avoided, and meanwhile, the retention of materials in a tank bottom pipeline is avoided. |
| Gear pump connection | 1. The gear pump is connected through a quick port, so that the gear pump can be easily disassembled for cleaning and maintenance while the tightness is guaranteed. |
| Reaction tank | 1. This tank is provided with two ports of compressed air and steam, so that device cleaning and online sterilization are effectively realized;<br>2. The tank bottom valve provides double-layer control of a manual valve and a pneumatic diaphragm valve to prevent materials from being discharged accidentally;<br>3. The feeding inlet of the reaction tank is in a bent-angle shape, so that liquid materials can flow into the tank along the wall, and the risk is reduced. |
| Oil filter tank | 1. This tank is connected to a vacuum pump and the tank bottom is a 316 L sieve having a pore size of 50 μm. Residual liquid can be quickly and effectively removed, and materials can be effectively retained;<br>2. The discharging port of the tank is at a certain height from the tank bottom, so that non-available materials can be effectively removed, and available materials can be used for subsequent process. |
| Washing tank | 1. It is provided with an injection water inlet, and injection water can be rapidly cooled to normal temperature by a heat exchanger and introduced into the tank;<br>2. The tank is connected to a vacuum pump and the tank bottom is a 316L sieve having a pore size of 50 μm. Residual liquid can be quickly and effectively removed, and materials can be effectively retained. |
| Control panel | 1. According to the tank system, all important parameters, such as opening, closing and adjustment of the rotating speed for stirring, turning on and off of the pneumatic diaphragm valve, and temperature detection, are all controlled on the control panel, so that the labor amount is greatly reduced. |
| Systematic sterilization of tanks | 1. The reaction tank, the washing tank, the water phase tank and the precooling tank are all provided with high-temperature high-pressure steam ports and controlled by pneumatic diaphragm valves, the whole tank system can realize online sterilization, and the sterilization duration and the sterilization temperature can be set through the control panel. |

1. Proportioning of an organic phase stock solution 1. Firstly, check the clean states of the mixing tank, the precooling tank, a liquid sterilization filter and a measuring tool and the site-clearing records, and allow to use if they are clean and within the site-clearing expiry date. Measure raw and auxiliary materials, and sequentially add a plurality of raw and auxiliary materials into the mixing tank by a peristaltic pump in a certain proportion. Open the mixing tank for stirring, set the rotating speed in the range of 10-150 rpm, and stirring for 0.5-4 h. Seal the tank, only keep the compressed air port open until the pressure inside the tank reaches 0.1-1 MP, pump the stock solution 1 into the liquid sterilization filter, and then feed it into the precooling tank, wherein the outer wall interlayer of the precooling tank is provided with a refrigerant liquid. Under the continuous cooling effect of a cooling-water machine, reduce the temperature of the stock solution 1 to 0° C. to −196° C. for later use, and in the meanwhile, keep stirring of the precooling tank at 10-2,000 rpm, and for 0.5-24 h.

The organic phase stock solution 1 is a mixed organic phase and contains an organic solvent and a nonionic surfactant, wherein the organic solvent is selected from at least one of hydrofluoroether, carbon tetrachloride, petroleum ether, cyclohexane, liquid paraffin, edible oil, soybean oil, olive oil, chloroform, dichloromethane, carbon tetrachloride and tetrachloroethylene, and the nonionic surfactant is selected from at least one of sorbitan fatty acid ester, fatty acid glyceride, laurate, alkylphenol polyoxyethylene ether, high-carbon fatty alcohol polyoxyethylene ether, arlacel, PO-500, polyoxyethylene sorbitan monooleate, and tween.

The refrigerant fluid includes, but is not limited to, at least one of liquid nitrogen, ethanol, trichloroethane, isopropanol, dichloromethane, ethyl acetate, ethylene glycol, propylene glycol, isobutane, n-hexane, chloroform, tetrahydrofuran, bromohexane and acetonitrile, and is cooled to 0° C. to −196° C. using a cryogenic refrigerator.

2. Proportioning of a stock solution 2. Firstly, check the cleanliness states of the water phase tank and the measuring tool and the site-clearing records, and allow to use if they are clean and within the site-clearing expiry date. Weigh raw materials, and pour the main stock solution 2-1 into the injection water to prepare a stock solution 2-1 liquid with a certain concentration and a certain volume. Add the stock solution 2-1 liquid into the water phase tank using the peristaltic pump, add a stock solution 2-2, set the rotating speed in the range of 10-300 rpm, and stirring the solution for 5-120 min.

The stock solution 2-1 contains a synthetic biological material and or a natural biological material, and a buffer solution.

The synthetic biological material is selected from at least one of polyethylene glycol, a polyethylene glycol derivative, polyethylene glycol diacrylate, polypropylene, polystyrene, polyacrylamide, polylactic acid, polyhydroxy acid, a polylactic acid-alcohol acid copolymer, polydimethylsiloxane, polyanhydride, polyacrylate, polyamide, polyamino acid, polyacetal, polycyanoacrylate, polyurethane, polypyrrole, polyester, polymethacrylate, polyethylene, polycarbonate, and a polyethylene oxide.

The natural biological material is selected from at least one of collagen, proteoglycan, glycoprotein, gelatin, a gelatin derivative, chitin, alginate, an alginate derivative, agar, fibrinogen, matrigel, a hyaluronic acid, laminin, and fibronectin.

The buffer solution includes at least one of carboxymethylcellulose, sodium chloride, polyacrylamide, potassium chloride, polyvinylpyrrolidone, sodium sulfate, calcium chloride, sodium chloride, sodium carbonate, and sodium bicarbonate.

The stock solution 2-2 includes, but is not limited to, divinylbenzene, diisocyanate, N-hydroxysuccinimide, N,N-methylenebisacrylamide, formaldehyde, glutaraldehyde, 1-(3-dimethylaminopropyl)-3-ethylcarbodiimide hydrochloride, calcium ions, tetramethylethylenediamine, ammonium sulfate, genipin, transglutaminase and the like.

3. Feed them into the reaction tank for mixing. Firstly, check the clean state and site-clearing records of the reaction tank, and allow to use if they are qualified. A refrigerant fluid flows in the outer wall interlayer of the reaction tank; the reaction tank is first acted continuously by a cooling-water machine, the temperature of the tank is reduced to 0° C. to −196° C., and after the temperature meets the requirements and the preparation of both the stock solution 1 and the stock solution 2 is completed, the stock solution 1 is mixed by a microsphere forming machine (i.e. the apparatus for preparing the emulsion) at a flow rate of 50-5,000 ml/min and pumped into the reaction tank. The stock solution 2 enters the reaction tank by the microsphere forming machine in a gas pressurization mode, and the pressure intensity of gas is 1-100 Kpa. The gas includes, but is not limited to, air, nitrogen, carbon dioxide, oxygen, argon and the like. Open the reaction tank for stirring, set the rotating speed in the range of 10 rpm to 1,200 rpm, and stirring the solution for 2-72 h.

The structure of the microsphere forming machine can be seen in FIG. 1 and can be separated into three portions:

The upper layer is a stock solution 2 chamber, the liquid flows in the vertical direction, and the stock solution 2 flows from top to bottom and is driven by an inert gas. The stable air pressure drives the stock solution 2 to flow through the multi-hole plate at a uniform speed from top to bottom in the vertical direction.

The middle layer is the multi-hole plate, the plate surface includes a large number of cut micro-wells, the diameter of the micro-wells ranges from 0.1 μm to 500 μm, and the cut plate can be in a shape of a single-layer sheet, a multi-layer sheet, a hollow tube, a hollow block and the like. The size of the micro-wells affects the diameter of formed emulsion droplets and the particle size of a final material, and the size of final microcarrier particles is about 5-20 times the diameter of the micro-wells.

The lower layer is a stock solution 1 circulating layer, and the liquid circulates in the horizontal direction. The stock solution 1 is driven by the gear pump, and the flow of the stock solution 1 is controlled to be 5-20 times that of the stock solution 2 vertically flowing through the cut plate in unit time. The flow rate will finally affect the stability of the formed emulsion. Any deviation from this range may cause a serious demulsification phenomenon.

The stock solution 2 flows from top to bottom, a stable gas pressure is provided through an external gas path at the upper portion of the water phase tank, the pressure intensity of gas can be set in the range of 1-100 Kpa with the stable interval of ±1 Kpa. The gas includes, but is not limited to, air, nitrogen, carbon dioxide, oxygen, argon and the like. Under the effect of the stable pressure intensity, the stock solution 2 stably passes through the multi-hole plate from top to bottom to form an initial liquid of circular liquid droplets. Meanwhile, the stock solution 1 flows through the lower portion of the multi-hole plate at a constant speed with the help of the gear pump, shears the stock solution 2 passing through the multi-hole plate into stable microsphere liquid droplets, and because the stock solution 1 and the stock solution 2 are immiscible with each other, stable microsphere liquid droplets composed of the stock solution 2 are formed and suspended in the stock solution 1. The particle size of the stock solution 2 microspheres is influenced by the diameter of a micro-well die on the cut micro-well plate, and 1-1,000 µm uniform liquid microspheres with particle size errors within the range of 100 µm can be prepared when the diameter of the micro-well die ranges from 0.1 µm to 500 µm.

4. Cleaning. Firstly, check the cleanliness states of the oil filter tank, the washing tank and the measuring tool and the site-clearing records, and allow to use if they are clean and within the site-clearing expiry date. Pump the reacted materials into the oil filter tank through the compressed air of 0.1-1 MP, and remove redundant liquid in the materials under the continuous effect of vacuum pump. After the above processes are finished, firstly add the cleaning agent, open the oil filter tank for stirring, and set the speed of 10-70 rpm to fully mix the materials with the cleaning agent. Turn off the stirrer for standing for 2-5 minutes, and then turn it on and set the speed at 20-50 rpm to fully mix the available materials with the cleaning agent. Use the compressed air of 0.1-1 MP to pump the available materials and the cleaning agent into the washing tank. Remove the cleaning agent in the washing tank through continuous effect of the vacuum pump. Add a certain volume of injection water with a certain temperature into the washing tank, and repeat washing for five times, wherein each stirring (washing) time is respectively 10 min to 24 h.

The cleaning agent includes, but is not limited to, acetone, anhydrous copper sulfate, calcium chloride, sodium sulfate, anhydrous ethanol, medical alcohol, hydrofluoroether, sodium alkylbenzene sulfonate, sodium aliphatic alcohol sulfate, sodium tripolyphosphate, deionized water and the like.

5. Freeze drying and sieving. Firstly, check the clean states of a freeze-drying box, the measuring tool and a freeze-drying machine and the site-clearing records, and allow to use if they are clean and within the expiry date. Mix the washed materials with injection water according to the wet weight in a certain proportion, freeze the mixture in a freezing device or a refrigerant fluid at −10° C. to −196° C., and transfer it to the freeze-drying machine for freeze drying for 12-96 hours after freezing. The pore size of micro-wells in the obtained three-dimensional porous microcarrier is 20-200 microns, and the porosity can reach 85-95%.

6. Tabletting and packaging. Firstly, check the clean state of a tabletting machine and the site-clearing records, and allow to use if it is clean and within the expiry date; add materials to be tabletted into the tabletting machine, and extruding independent tablets with the same quality and consistent shape by setting various parameters of the device. The properties of tablets, such as water absorption, dispersibility and stability, may be observed, recorded and tested in real time during tabletting. The prepared tablets can be filled into corresponding packaging bottles according to a certain amount in time, and subsequent operations such as inspection can be applied after the packaging is finished.

The process for preparing microcarrier particles of the present disclosure is further illustrated by the following specific examples.

Example 1

Oil Phase Proportioning 1.1 Firstly, check the clean states of a mixing tank, a precooling tank, a liquid sterilization filter and a measuring tool and the site-clearing records, and allow to use if they are clean and within the site-clearing expiry date;

1.2 Sequentially add 100 L of petroleum ether and 10 L of PO-500 reagent into the mixing tank by using a peristaltic pump. Open the mixing tank for stirring, set the rotating speed at 60 rpm, and stirring for 1 hour;

1.3 Seal the mixing tank, only keep a compressed air port open until the pressure inside the tank reaches 0.1 MP, and then pump an oil phase into the precooling tank. Reduce the temperature of the oil phase to −10° C. for later use under the continuous cooling effect of a cooling-water machine, and meanwhile, keep the stirring speed of the precooling tank at 40 rpm.

Water Phase Proportioning 2.1 Firstly, check the clean states of a water phase tank and a measuring tool and the site-clearing records, and allow to use if they are clean and within the site-clearing expiry date.

2.2 Weigh 100 g of gelatin, put into 5 L of deionized water, use a stirrer with a set speed of 60 rpm to stir the gelatin solution until it is fully dissolved, add the gelatin solution into the water phase tank by using a peristaltic pump, set the rotating speed at 150 rpm, and stirring the solution for 90 minutes for later use;

Mixing 3.1 Firstly, check the clean state of a reaction tank and the site-clearing records, and allow to use if they are qualified;

3.2 Under the continuous effect of the cooling-water machine, reduce the temperature of the tank to −10° C. or below. When the temperature of the reaction tank meets the requirements, the temperature of the oil phase reaches −10° C., add 5 mL of 75% formaldehyde solution into the water phase, set the rotating speed at 80 rpm, stirring for 10 minutes, later mix the oil phase and the water phase through a microsphere forming machine, and then feed the mixture into the reaction tank. The oil phase is driven by the gear pump (having a pumping speed of 3,000 mL/min), the water phase is driven by the inert gas with fixed pressure intensity (air is selected as the gas), and the pressure intensity is set as 5 KPa. A multi-hole plate selected for the microsphere forming machine has a well size of 30 µm.

The microsphere forming machine is composed of a cuboid with the size of 40 cm*40 cm*30 cm, a plastic plate with the size of 40 cm*40 cm and the thickness of 1 cm is horizontally arranged, at the position of 1 cm above an oil phase inlet and an outlet of the forming machine, in the forming machine. A large number of round through wells with the diameter of 30 µm are formed in the plastic plate by a micro-machining technology to form a micro-well array of 300*300, with the spacing of micro-wells of 50 µm. The dispersed phase (water phase) flows, perpendicular to the micro-well plate, into the microsphere forming machine and vertically penetrates the micro-well plate through the micro-wells on the plate, the oil phase solution below the micro-well plate rapidly flows into the microsphere forming machine from the horizontal inlet and continuously and rapidly shears the water phase solution passing through the micro-wells to form microspheres, and the formed microspheres are dispersed in the oil phase and flow out from the horizontal outlet.

3.3 After materials enter the reaction tank, turn on the stirrer immediately, set the rotating speed at 30 rpm, and enabling stirring reaction for 48 h.

Cleaning 4.1 Firstly, check the clean states of an oil filter tank, the washing tank and the measuring tool and the site-clearing records, and allow to use if they are clean and within the site-clearing expiry date;

4.2 Pump the reacted materials into the oil filter tank by using 0.15 MP of compressed air, remove redundant liquid in the materials under the continuous effect of the vacuum pump, then add a cleaning agent into the materials, namely 50 L of acetone, 10 kg of calcium chloride, 100 L of medical alcohol and 100 L of absolute ethyl alcohol, set the stirrer at a rotating speed of 100 rpm, respectively stir them for 20 min, and carry out suction filtration on the redundant liquid by the vacuum pump after each cleaning. Pump the available materials and the alcohol into the washing tank by using 0.10 MP of compressed air;

4.3 Add 20 L of deionized water into the washing tank, set the stirrer at a rotating speed of 100 rpm, fully stir the solution for 50 min, and remove the injection water under the effect of the vacuum pump. Repeat washing for 3-5 times.

Freeze Drying 5.1 Firstly, check the clean states of a freeze-drying box, the measuring tool and a freeze-drying machine and the site-clearing records, and allow to use if they are clean and within the expiry date;

5.2 Add 50 g of the washed material by wet weight and 500 mL of the injection water into the freeze-drying box for mixing. Freeze them at −20° C. for 48 h.

5.3 Put frozen materials into the freeze-drying machine, carry out freeze drying according to the operating procedure of the freeze-drying machine, and continuously carry out freeze drying for more than 72 h. Weigh the total weight of freeze-dried materials, and transfer them to a temporary material storage box for the next process.

Sieving 6.1 Firstly, check the clean states of a sieve and a sieving machine and the site-clearing records, and allow to use if they are clean and within the expiry date;

6.2 Sieve the freeze-dried materials according to the size range of 50-500 microns. Collect the sieved materials to obtain porous microcarrier particles within a certain particle size range.

Figure 4:
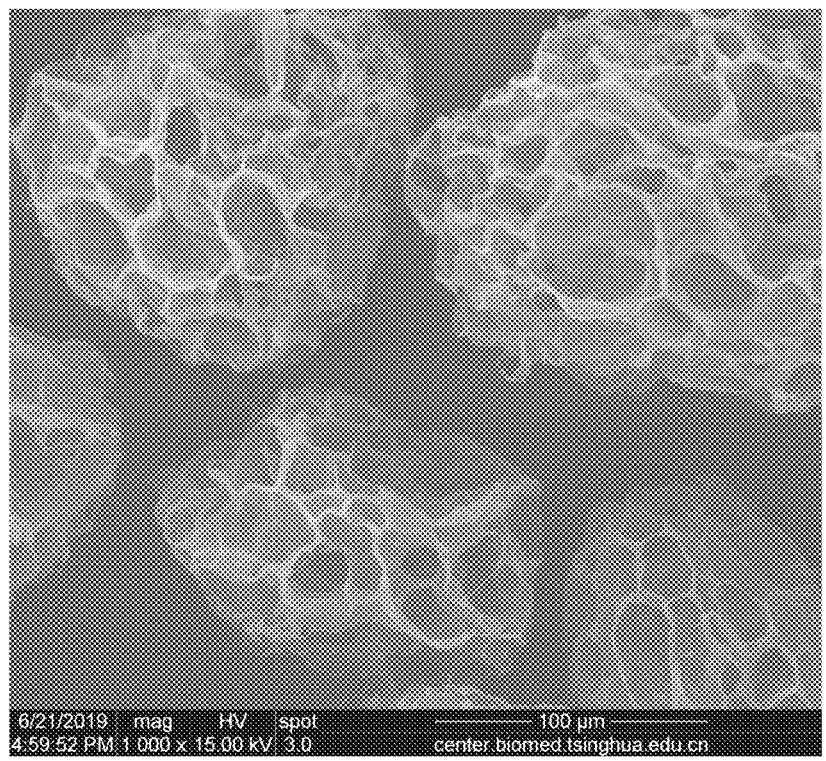
FIG. 4 shows an electron micrograph of microcarrier particles prepared in Embodiment 1.

Results: The obtained microcarrier has an average particle size of 200 μm and a pore size of 25 μm, reaching the porosity of 80%. The yield was about 50 g, reaching the yield of 50%. An electron micrograph taken by placing the microcarrier in a water solution is as shown in FIG. 4.

Example 2

Oil Phase Proportioning 1.1 Check devices as in Example 1 above;
1.2 Measure 80 L of trichloromethane, 20 L of petroleum ether and 10 L of Tween 20 reagent and sequentially add them into the mixing tank by using the peristaltic pump. Open the mixing tank for stirring, set the rotating speed at 60 rpm, and stirring for 1 h;
1.3 Seal the mixing tank, only keep a compressed air port open until the pressure inside the tank reaches 0.1 MP, and then pump an oil phase into the precooling tank. Reduce the temperature of the oil phase to −30° C. for later use under the continuous cooling effect of a cooling-water machine, and meanwhile, keep the stirring speed of the precooling tank at 40 rpm.

Water Phase Proportioning 2.1 Check devices as in Example 1 above;
2.2 Weigh 50 g+ of gelatin and 10 g of sodium alginate, put them into 1.5 L of deionized water, use the stirrer with a set speed of 60 rpm to stir the gelatin solution until they are fully dissolved, add the mixture into the water phase tank by using the peristaltic pump, then add 100 g of sodium chloride, heat the mixture to 60° C., set the rotating speed at 150 rpm, and then stir the mixture for 120 minutes for later use;

Mixing 3.1 Check devices as in Example 1 above;
3.2 Under the continuous effect of the cooling-water machine, reduce the temperature of the tank to −30° C. or below. The lower the temperature is, the smaller the pore size of the prepared carrier material is, and the pore size of the microcarrier prepared at −30° C. is about 5-20 μm. After the temperature is reduced to a preset temperature, add 5 ml of 75% formaldehyde solution into the water phase, set the rotating speed at 80 rpm, stir the water phase for 5 minutes, and then mix the oil phase and the water phase through the microsphere forming machine at a certain flow rate and pump the mixture into the reaction tank. The oil phase is driven by the gear pump (having a pumping speed of 1,000 ml/min); the lower the pumping speed is, the larger the particle size of the prepared granular material is, and otherwise the smaller the particle size is. The average particle size of the prepared material under these conditions is about 400 μm. The pressure intensity of nitrogen pressurization for driving the water phase is set to 10 KPa. The greater the pressure intensity is, the larger the particle size of the microspheres is, and vice versa. The average particle size under these conditions is 400 μm. A multi-hole plate selected for the microsphere forming machine has a well size of 50 μm.

The microsphere forming machine used is the same as that in Example 1 except that the multi-hole plate has a well size of 50 μm.

3.3 After materials enter the reaction tank, turn on the stirrer immediately, set the rotating speed at 30 rpm, enabling stirring reaction for 48 h, and meanwhile, regularly observe and record the reaction state of materials in the tank and various parameters.

Cleaning 4.1 Check devices as in Example 1 above;
4.2 Pump the reacted materials into the oil filter tank by using 0.15 MP of nitrogen, remove redundant liquid in the materials under the continuous effect of the vacuum pump, then add a cleaning agent into the materials, namely 50 L of acetone, 20 kg of anhydrous magnesium sulfate, 100 L of medical alcohol and 100 L of absolute ethyl alcohol, set the stirrer at a rotating speed of 300 rpm, respectively stir them for 20 min, and carry out suction filtration on the redundant liquid by the vacuum pump after each cleaning. Pump the available materials into the washing tank by using 0.10 MP of compressed air;
4.3 Add 20 L of deionized water into the washing tank, set the speed at 100 rpm, fully stir the solution for 50 min, and remove the injection water under the effect of the vacuum pump. Repeat washing for 3-5 times.

Freeze Drying 5.1 Check devices as in Example 1 above;
5.2 Add 50 g of the washed material by wet weight and 300 mL of the injection water into the freeze-drying box for mixing. Freeze them at −40° C. for 96 h.
5.3 Put frozen materials into the freeze-drying machine, carry out freeze drying according to the operating procedure of the freeze-drying machine, and continuously carry out freeze drying for more than 72 h. Weigh the total weight of freeze-dried materials, and transfer them to a temporary material storage box for the next process.

Sieving 6.1 Firstly, check the clean states of a sieve and a sieving machine and the site-clearing records, and allow to use if they are clean and within the expiry date;
6.2 Sieve the freeze-dried materials according to the size range of 50-500 microns. Collect the sieved materials to obtain a porous microcarrier within a certain particle size range.

Figure 5:
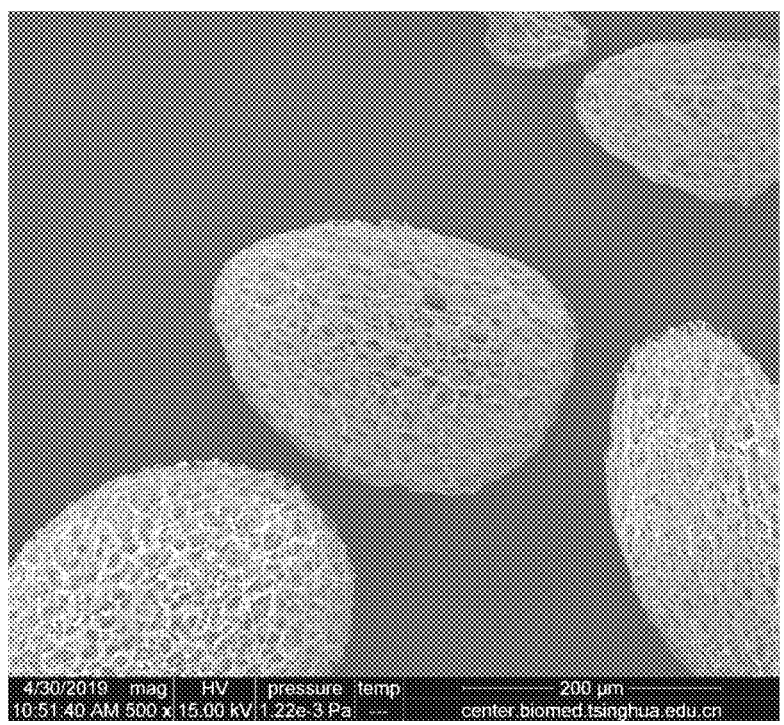
FIG. 5 shows an electron micrograph of microcarrier particles prepared in Embodiment 2.

Results: The obtained microcarrier has an average particle size of 400 μm and a pore size of 15 μm, reaching the porosity of 90%. The yield was about 20 g, reaching the yield of 30% approximately. An electron micrograph taken by placing the microcarrier in a water solution is as shown in FIG. 5.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for preparing microcarrier particles, comprising the steps:
   1) preparing a dispersed phase liquid and a continuous phase liquid, wherein:
      the dispersed phase liquid contains a synthetic polymer and/or natural biological macromolecules, and a curing agent;
      the continuous phase liquid contains an organic solvent and a nonionic surfactant;
   2) allowing the dispersed phase liquid to flow from one side of a multi-hole plate to the other side of the multi-hole plate through a plurality of micro-wells of the multi-hole plate while allowing the continuous phase liquid to flow, parallel to the multi-hole plate, on the other side of the multi-hole plate, shearing the dispersed phase liquid passing through the multi-hole plate to form liquid microspheres in the flowing continuous phase liquid;
   3) allowing the synthetic polymer and/or the natural biological macromolecules in the liquid microsphere to react with the curing agent to form particles; and
   4) collecting and washing the particles;
   wherein, the temperature of the continuous phase liquid in Step 2) does not exceed 0° C.; and Step 3) is executed for 2-72 hours at the temperature of not higher than 0° C.

2. The method of claim 1, wherein Step 2) is executed in a vessel comprising the multi-hole plate which separates the interior of the vessel into a first portion and a second portion, the dispersed phase liquid enters the first portion through a dispersed phase inlet arranged on the vessel and connected with the first portion and then flows into the second portion through the multi-hole plate; the continuous phase liquid enters the second portion through a continuous phase inlet arranged on the vessel and connected with the second portion; the mixed liquid containing the liquid microspheres after the dispersed phase liquid and the continuous phase liquid are mixed leaves the vessel through an outlet arranged on the vessel and connected with the second portion; and the vessel outlet and the continuous phase inlet are arranged on the opposite sides of the vessel.

3. The method of claim 2, wherein the dispersed phase liquid enters the first portion of the vessel and flows through the multi-hole plate by gas pressurization; the continuous phase liquid enters the second portion of the vessel by a gear pump and flows parallel to the multi-hole plate.

4. The method of claim 1, wherein Step 3) is performed in a tank provided with a stirring device.

5. The method of claim 1, wherein Step 4) is performed by vacuuming in a tank provided with a filtering device.

6. The method of claim 1, wherein the micro-wells have a diameter between 0.1 μm and 500 μm.

7. The method of claim 1, wherein the micro-wells have a diameter between 30 μm and 50 μm.

8. The method of claim 1, wherein the flow of the continuous phase liquid is 5-20 times that of the dispersed phase liquid over the same time.

9. The method of claim 1, wherein the synthetic polymer is selected from at least one of polyethylene glycol, a polyethylene glycol derivative, polyethylene glycol diacrylate, polypropylene, polystyrene, polyacrylamide, polylactic acid, polyhydroxy acid, a polylactic acid-alcohol acid copolymer, polydimethylsiloxane, polyanhydride, polyacrylate, polyamide, polyamino acid, polyacetal, polycyanoacrylate, polyurethane, polypyrrole, polyester, polymethacrylate, polyethylene, polycarbonate, and a polyethylene oxide; the natural biological macromolecules are selected from at least one of collagen, proteoglycan, glycoprotein, gelatin, a gelatin derivative, chitin, alginate, an alginate derivative, agar, fibrinogen, matrigel, a hyaluronic acid, laminin, and fibronectin; and the curing agent is selected from at least one of divinylbenzene, diisocyanate, N-hydroxysuccinimide, N,N-methylenebisacrylamide, formaldehyde, glutaraldehyde, 1-(3-dimethylaminopropyl)-3-ethylcarbodiimide hydrochloride, calcium ions, tetramethylethylenediamine, ammonium sulfate, genipin, and transglutaminase.

10. The method of claim 1, wherein the organic solvent is selected from at least one of hydrofluoroether, carbon tetrachloride, petroleum ether, cyclohexane, liquid paraffin, edible oil, soybean oil, olive oil, chloroform, dichloromethane, carbon tetrachloride, and tetrachloroethylene; and the nonionic surfactant is selected from at least one of sorbitan fatty acid ester, fatty glyceride, laurate, alkylphenol polyoxyethylene ether, high-carbon fatty alcohol-polyoxyethylene ether, arlacel, PO-500, polyoxyethylene sorbitan monooleate, and tween.

11. The method of claim 1, wherein the dispersed phase liquid further contains a buffer agent selected from at least one of carboxymethylcellulose, sodium chloride, polyacrylamide, potassium chloride, polyvinylpyrrolidone, sodium sulfate, calcium chloride, sodium chloride, sodium carbonate, and sodium bicarbonate.

12. The method of claim 1, wherein the ratio of the organic solvent to the nonionic surfactant in the continuous phase liquid is from 5:1 to 20:1 by weight.

* * * * *